United States Patent [19]
Korpman

[11] Patent Number: 4,731,066
[45] Date of Patent: Mar. 15, 1988

[54] ELASTIC DISPOSABLE DIAPER

[75] Inventor: Ralf Korpman, Bridgewater, N.J.

[73] Assignee: Personal Products Company, Milltown, N.J.

[21] Appl. No.: 12,984

[22] Filed: Feb. 10, 1987

Related U.S. Application Data

[63] Continuation of Ser. No. 595,181, Mar. 30, 1984, abandoned.

[51] Int. Cl.$^4$ ............................................. A61F 13/16
[52] U.S. Cl. ..................................... 604/366; 604/370
[58] Field of Search ................. 604/385.1, 385.2, 366, 604/370, 372, 373, 369, 367; 128/155, 156

[56] References Cited

U.S. PATENT DOCUMENTS

| | | | |
|---|---|---|---|
| 3,779,246 | 12/1973 | Mesek et al. | 604/370 |
| 4,041,949 | 8/1977 | Kozak | 604/370 |
| 4,166,464 | 9/1979 | Korpman | 604/370 |

*Primary Examiner*—John D. Yasko

[57] ABSTRACT

The invention provides an elastic laminated disposable diaper which has a liquid-impermeable backing which is produced from an initially molten extruded elastic film, an absorbent core and a liquid-permeable facing. The facing is at least about 25 percent extensible and is coextensive with the backing. The absorbent unit being laminated between the facing and the backing.

4 Claims, 5 Drawing Figures

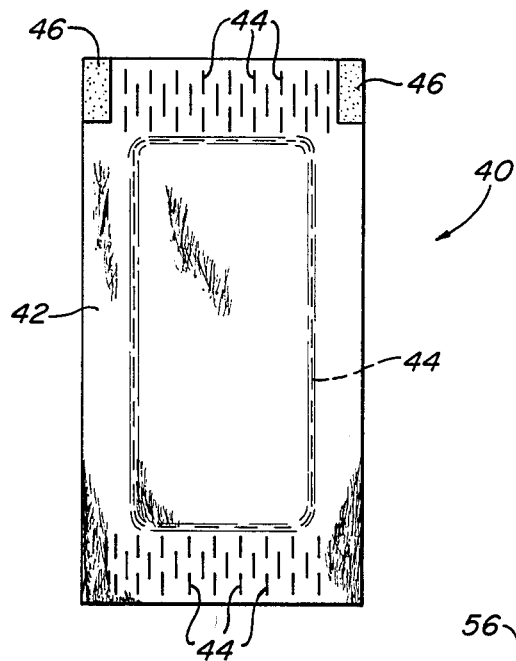
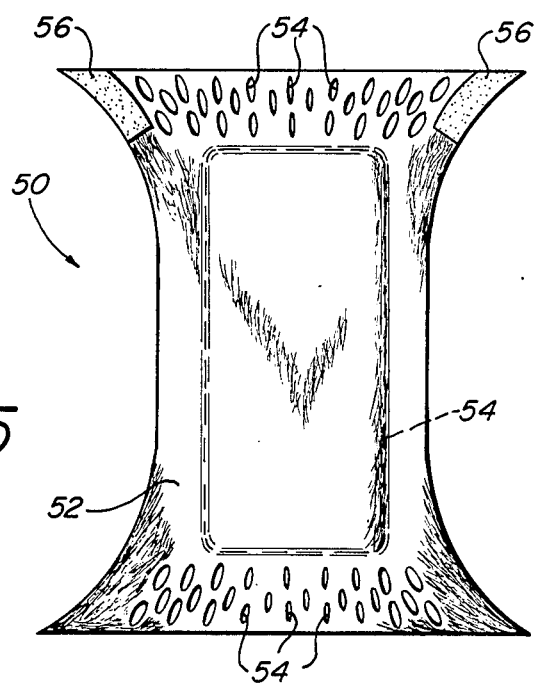

ELASTIC DISPOSABLE DIAPER

This is a continuation of application Ser. No. 595,181, filed Mar. 30, 1984, now abandoned.

BACKGROUND OF THE INVENTION

The present invention relates to a disposable elastic diaper which includes an initially molten film having laminated thereto an absorbent unit and an extensible fabric.

Disposable diapers, sanitary napkins, incontinent pads, and similar disposable articles have become commercially important. The structure of these articles is similar and generally has three basic components: a liquid-impermeable backing, an absorbent unit and a liquid-permeable facing. Generally, the backing is of a film such as a polyethylene film and typical prior art diapers are shown in U.S. Pat. No. Re. 26,151 and U.S. Pat. No. 3,612,055. Generally, the absorbent unit is smaller in size than the backing or the facing and is sandwiched between the backing and the facing, the latter two being laminated one to the other in the marginal portions. Frequently, the absorbent unit is a fluff batt of loosely compacted cellulosic fibers, such as woodpulp fibers.

Though the backing film, typically of polyethylene film, is liquid-impermeable it is frequently noisy and has a very slick feeling to it. Furthermore, the thin polyethylene films that are used tend to tear rather easily. Many attempts have been made to overcome these drawbacks. For instance, a diaper having a fibrous outer layer is shown in U.S. Pat. No. 3,779,246. All diapers formed in accordance with this patent have improved feel and appearance as compared to diapers having an exposed plastic sheet as the outermost layer. The fabric layer coupled with the necessary adhesive introduces additional thickness which in turn can impair flexibility.

Another problem with commercially available disposable diapers is the stability of the fluff batt. Many improvements have been made to stabilize the fluff batt. For instance, in U.S. Pat. No. 3,017,304 a paper-like densified skin is provided on the outermost side of the fluffed batt and in U.S. Pat. No. 3,938,522 densified regions, generally in the form of embossed lines, are present to both stabilize the fluff batt and to promote wicking. Whereas these techniques resulted in an improved product, the paper-like densified skin and/or the densified regions tend to stiffen the fluff batt and it is known that the densified regions are of reduced liquid holding capacity.

All of the known disposable diapers are laminated products wherein adhesive or glue is required to adhere one layer of the product to another layer. The adhesive or glue also lends thickness to the product and hence can make the product less flexible. Furthermore, the adhesive or glue detracts from the absorbent capacity of the product. In addition, the products that have been made do not have extensibility. Consequently, several sizes are necessary for each product line so that as the infant grows, or in the case of an adult product, the varying sizes can be accommodated in a product that is of an appropriate size.

Attempts have been made to place elastic in disposable diaper products both to improve the fit and to permit a wider range of sizes to be accommodated by one product line. Though products with elasticized leg portions have appeared in the marketplace the basic problem of having to provide several sizes in a product line has not been overcome. Furthermore, the products currently in the marketplace are made with adhesive lines or glue lines in order to satisfactorily laminate the product.

The present invention provides a product with a cloth-like backing which can be extended to accommodate more than one size.

SUMMARY OF THE INVENTION

The present invention provides an elastic laminated disposable diaper which has a liquid-impermeable backing comprised of an initially molten extruded elastic film. The diaper has an absorbent core and a liquid-permeable facing comprised of fabric having at least 25% extensibility and which is coextensive with said backing. The absorbent core is laminated between the facing and the backing. Preferably, the liquid-impermeable backing of initially molten elastic film has laminated to it an extensible fabric on the outside to provide a cloth-like feel to the product. The absorbent unit is of smaller dimension than the facing and backing and is sandwiched between the two, wherein the facing is laminated to the backing around the periphery of the absorbent unit. The fabric used in the present invention has an extensibility of at least about 25%, preferably about 50% to 100%. The extensibility need not be in the fabric in both directions but, when the fabric is placed on the disposable diaper of the present invention the extensibility is in the transverse direction.

The initially molten film which provides the liquid barrier, or at least a portion of the backing, is an elastic film which is extensible from about 400–3000%.

The combination of the extensibility of the film and of the fabric permits use of a diaper product for fit on a wider range of sizes.

In a preferred embodiment of the present invention, an initially molten elastic film has a cloth or a fabric which is extensible transversely laminated to one side thereof. On the other side, the film has an absorbent unit smaller in size with a liquid-permeable extensible fabric covering the absorbent unit and coterminous with the film. The liquid-permeable fabric is laminated to the film around the periphery of the absorbent unit. An absorbent structure thereby is provided which is thin, highly flexible, extensible transversely, highly absorbent and optionally has fabric on both sides thereof. Furthermore, the present invention provides a product wherein all components of the product are stabilized and a moisture barrier is provided without the use of glues or adhesives.

BRIEF DESCRIPTION OF THE DRAWINGS

FIG. 4 is a plan view of another embodiment of the present invention; and

FIG. 5 is a plan view of the embodiment of FIG. 4 in its extended position.

DETAILED DESCRIPTION OF THE INVENTION

Figure 1:
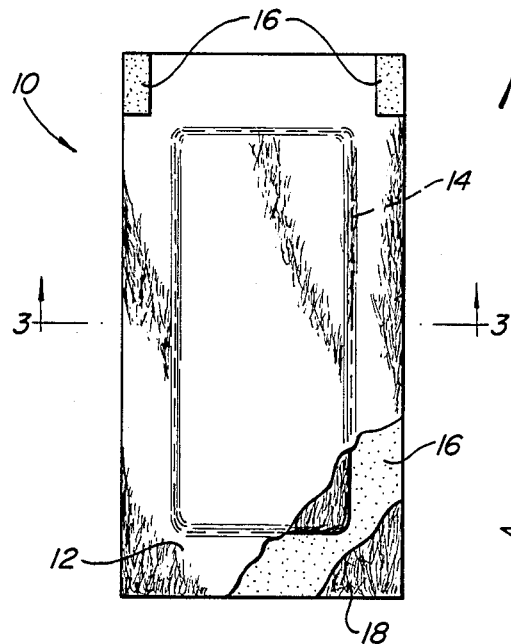
FIG. 1 is a plan view of one embodiment of the present invention.
Figure 2:
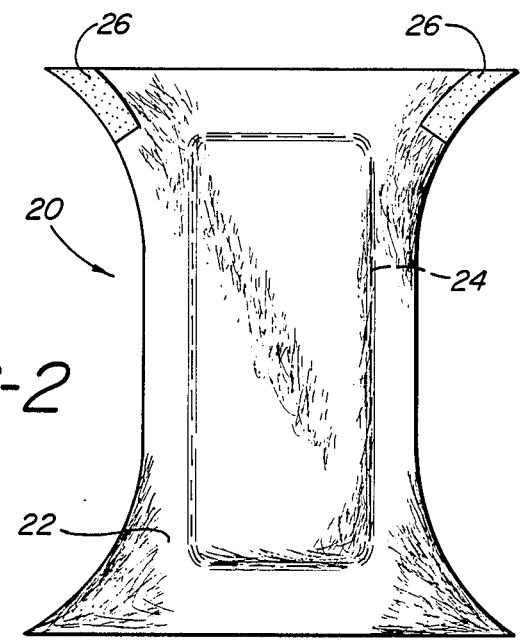
FIG. 2 is a plan view of the embodiment of FIG. 1, with the waist portions extended.

Referring now to the drawings, FIG. 1 illustrates a disposable diaper 10. The disposable diaper 10 has a cloth facing 12 which is a soft, thin, extensible fabric. The absorbent unit 14 is substantially centrally located and is covered by facing 12 on one side and an initially molten elastic film on the other side, below the initially molten film is another layer of fabric. In two of the corners at one end are adhesive masses 16 which form the necessary securement means for securing the product about the waist of the wearer. FIG. 2 illustrates the embodiment of FIG. 1 in its extended position wherein the waist regions at each end have been extended. The diaper product 20 has a facing 22 and an absorbent unit 24. The securement adhesive regions 26 are located in the corners at one of the extended ends.

Figure 3:
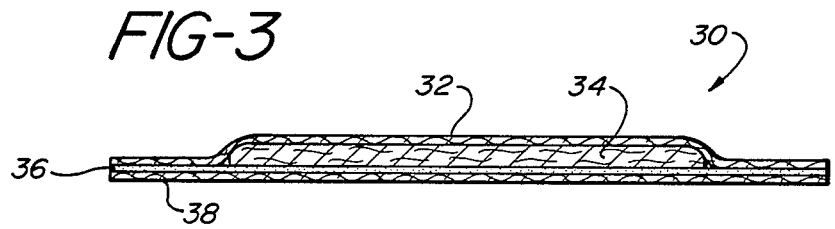
FIG. 3 is a cross-sectional view taken along lines 3—3 of FIG. 1.

FIG. 3 is a cross-sectional view along lines 3—3 of FIG. 1 illustrating the layered structure of the present invention. The product 30 has a facing 32 which is an extensible fabric. The absorbent unit 34 is substantially centrally located and is held in place by its contact with the initially molten elastic film 36. Similarly, the fabrics 32 and 38 are bonded to the initially molten elastic film 36.

Another embodiment is illustrated in FIG. 4 wherein a disposable diaper 40 has a facing fabric 42 having parallel and staggered rows of slits 44 placed at each end of the fabric on the diaper facing. Similarly, if there is a fabric on the underside of the diaper, slits are also present in order to provide the necessary expansion of the fabric when the diaper is extended, as illustrated in FIG. 5, to provide the necessary width to fasten the product around the waist of the wearer. The diaper 40 has closure means 46 in the form of pressure-sensitive adhesive regions at one end of the product. In FIG. 5 the diaper 50 is illustrated in its extended form wherein the product has a facing 52 whereby the slits have been opened and form apertures 54 to permit the film to extend. The closure means 56 are the same pressure-sensitive adhesive regions as in FIG. 4.

The product of the present invention minimally is comprised of an initially molten elastic film, an absorbent unit and a fabric or liquid-permeable film. The initially molten film, which is elastic, is extruded to provide a thin, tacky film to which the absorbent unit and fabric (or film) are laminated while the film is tacky. Suitable films, for providing the initially molten elastic film, are one of four types of elastic films.

The first group of suitable materials for films which can be extruded to make the products of the present invention are the thermoplastic elastomeric films. One type which is suitable is an ethylene-vinyl acetate film wherein the vinyl acetate content is high, i.e., from about 40 percent to about 60 percent and the ethylene content is low. Another suitable type is polyurethane. The thermoplastic polyurethane elastomers are prepared from a high molecular weight di-primary diol, a low molecular weight chain extender, and a di-isocyanate. This combination is melt polymerized to form block copolymers with alternating hard and soft segments. The diol is either a polyester or a polyether. Generally, when such a polyurethane is extruded, a single stage extruder is used at temperatures of 320°-430° F.

Polyolefin blends are also suitable to provide a thermoplastic elastomer. These olefinics are blends of a hard component, generally a crystalline polyolefin such as polypropylene or polyethylene, and a soft portion composed of ethylene-propylene rubber. Generally, these olefinic thermoplastic elastomers are extruded at temperatures of 350°-450° F.

Some copolyesters are found to be elastomeric and can be used. Included in these is poly(ethylene terephthalateco-ethylene azelate). Elastomeric copolyester products can be formed from non-elastomeric copolyesters. For instance, poly(butylene terephthalate-co-butylene isothalate) copolyester composition can be blended in an amount of about 30 percent by weight with about 70 percent by weight of an elastomer. This alloy is then extruded and can be hot drawn to produce the ester modified elastomeric film.

Particularly suitable thermoplastic elastomers are the thermoplastic elastomeric block copolymers having thermoplastic end blocks and rubbery mid blocks which are designated as A-B-A block copolymers. The expression "A-B-A" block copolymer is intended to embrace all variations of block copolymers with rubbery mid blocks and thermoplastic end blocks. It is also intended to embrace radial block copolymers which may be designated $(A-B)_nX$, wherein X is a poly functional atom or molecule and in which each (A-B) radiates from X in a way that A is an end block. A-B block copolymers sometimes referred to as "simple" block copolymers, in which B forms one end block rather than a mid block, may be included to modify the A-B-A block copolymers and the expression "block copolymer" without qualification is intended to embrace them as well.

The thermoplastic "A" block is generally a polymer of alkenylarenes preferably of styrene or styrene homologues and analogues. The rubbery "B" block is a polymer of a conjugated aliphatic diene of from four to six carbon atoms or a lower alkene of from two to six carbon atoms. Suitable dienes include butadiene, isoprene, and the like. Suitable alkenes include ethylene, butylene, propylene, and the like. In the A-B block copolymers, the B blocks are preferably isoprene. The block copolymers may be linear branched or radial. A branched copolymer is essentially a linear polymer in which branching may occur randomly anywhere in the rubber copolymer chain. A radial block copolymer is characterized and distinguished from the branched linear copolymer in having blocks radiating from a central core.

The individual A block portion has a number average molecular weight of at least 6,000 preferably in the range of from about 8,000 to 30,000, and the B block portion has a number average molecular weight preferably in the range of from about 45,000 to about 180,000. The A block constitute from about five to about 50 percent of the block copolymer. The total block copolymer average molecular weight generally ranges from about 75,000 to about 200,000 for linear copolymers and from about 125,000 to about 400,000 for radial copolymers. In the A-B copolymers, the total molecular weight generally should not exceed about 150,000.

When the "A" block is polystyrene and the "B" block is a polymer of butadiene in an A-B-A type block copolymer, the polymer is frequently referred to as a S-B-S polymer and when the "A" block is a styrene polymer and the "B" block is an isoprene polymer, the polymer is frequently referred to as a S-I-S polymer. Examples of commercially available block copolymers include Solprene 1205 which is a simple S-B (Phillips Petroleum Company) and Shell Chemical Company's Kraton 1102 which is a linear S-B-S and 1107, 1112, and 1117 which are all linear S-I-S.

The elastomeric component of these thermoplastic elastomers may include small amounts of more conventional elastomers but these should not exceed about 25 percent by weight of the elastomeric component. These elastomers may include highly broken down natural rubbers and butadienestyrene random copolyner rubbers, synthetic polyisoprene, cloroprene rubbers, nitrile rubbers, butyl rubbers, and the like. Potentially elastomeric liquid polymers also may be employed as additives but normally in lower proportions not above about 10 percent by weight of the elastomeric component.

The second group of suitable film forming materials includes alloys which are physical mixtures of structurally different homopolymers or copolymers. Suitable alloys include a mixture of polyethylene and the block copolymers of the thermoplastic elastomer group. Also, polystyrene can be mixed with the block copolymers wherein a high proportion of the block copolymer will be used with a small amount of polystyrene. In addition, copolyesters with elastomers are suitable as taught in U.S. Pat. No. 4,389,444.

The third group of suitable film forming materials is a mixture of a thermoplastic elastomer and a low molecular weight (less than 3000) resin modifier. The thermoplastic elastomer is a linear or radial A-B-A block copolymer or mixture of the A-B-A copolymer with one or more simple A-B block copolymers. The A blocks are derived from styrene or styrene homologues and the B blocks are derived from conjugated dienes or lower alkenes. The low molecular weight resins generally are based on polyalphamethylstyrene, polystyrene, polyvinyltoluene and similar aromatic resins. Also included as suitable resins are copolymers thereof, coumarone indene, and related cyclic compounds. The resins are present in an amount of about 10 to about 200 parts for each 100 parts of thermoplastic elastomer. In addition to these resins, small proportions of other resins, i.e., not above about 25% by weight of the elastomeric component, may be added. These resins include hydrocarbon resins, rosin, hydrogenated rosin, rosin esters, polyterpene resins and the like. The resulting films are highly elastic and have a relatively low rubber modulus. The films generally possess high friction properties and are very flexible, extensible, soft and normally exhibit a Gurley stiffness of less than about one at a thickness of one mil.

The last group of suitable films are the pressure-sensitive adhesive films. These films include the hot melt adhesive films. The thermoplastic rubber block copolymers provide suitable formulations for pressure-sensitive adhesive film-formers which can be extruded to produce a highly desirable product. The elastomer will be of a high molecular weight and the resin a low molecular weight. A typical formulation is from 0 to 75 parts by weight of a tackifier resin in proportion to 100 parts by weight of a thermoplastic elastomeric component. Suitable tackifier resins include rosin and rosin derivatives of the abietic acid type or the pimaric acid type. The rosin acids react with alcohols to form esters, e.g., hydrogenated glycerine esters. Hydrocarbon tackier resins are suitable and include low molecular weight polymers containing primarily aromatic, aliphatic or diene monomers. An example of an aliphatic-monomer containing resins is one identified as Wing Tack 95 manufactured and sold by Goodyear Tire and Rubber Company. The terpene resins such as Piccolyte S-100 manufactured and sold by Hercules Chemical Company are also suitable.

Acrylate copolmers are also highly satisfactory. For example, methylmethacrylate-butadiene-styrene provide a suitable film-forming material. Polyacrylates of a proper monomer composition are inherently pressure-sensitive without any compounding. This single component feature has some advantages over the compounded adhesives. Low molecular weight ingredients that can migrate to the surface of an adhesive coating are absent. Adhesive bond is a surface phenomenon, and minimizing the compositional variations is difficult to avoid in multiphase systems, while uniformity is more easily achieved in single component adhesives.

Polyacrylates possess some inherent properties superior to many other polymers used for pressure-sensitive adhesives. The polymer is saturated and resistant to oxidation. It is water white and does not yellow on exposure to sunlight. The resistance to oxidation surpasses that of most polymers used for pressure-sensitive adhesives, except silicones. Monomers with various functional groups can be introduced during polymerization, and an adhesive with various degrees of thermosetting properties can be prepared.

Acrylic adhesives are available as solutions, aqueous emulsion melts, and 100% reactive solids.

A third type of pressure-sensitive adhesive film involves an ethylene-vinyl acetate based system wherein a tackifying resin is present. Generally the ethylene vinyl acetate copolymer is a random copolymer containing from about 40% to about 60% vinyl acetate by weight. The ethylene vinyl acetate polymer may be used singly or as a mixture with A-B-A or A-B block copolymers. Suitable tackifying resins include rosins and hydrogenated rosins and mixtures thereof.

Suitable film-formers are discussed in the following U.S. Pat. Nos.: 3,783,072; 3,932,328; 3,984,509; 4,080,348; 4,178,337; 4,379,806; 4,389,444; and 4,301,255.

The film forming composition may contain relatively small proportions of various other materials such as, antioxidants, heat stabilizers, ultra violet absorbers, release agents, extenders, plastizisers, pigments, fillers, and the like.

The film formers discussed above can be extruded as a foam as well as a continuous film. Generally a closed cell foam is preferred so that the foam is liquid-impermeable.

Suitable extruding techniques include the single screw extrusion and coextrusion techniques. The primary object being to provide a thin film which, at least in its molten form, is tacky. Of course, the pressure-sensitive adhesive films are still tacky after formation.

The absorbent unit of the present invention is smaller in size than the film so as to leave marginal regions surrounding the film to permit lamination of the facing fabric which covers the absorbent unit in those margin areas.

The absorbent unit is typically a fluff batt such as that used in conventional disposable diapers. Alternatively, the absorbent unit is a self-contained unit such as a compressed composite unit comprising a resilient fiber fabric, containing superabsorbent and a layer of wood pulp fibers, or the like, which has been compressed to form a highly absorbing unit. Still another form of an absorbent unit is a fabric which contains superabsorbent. All of the absorbent units are capable of absorbing at least about 5 milliliters per gram of the absorbent unit weight.

If the absorbent unit is a fluff batt, generally it is formed of hydrophilic fibers such as rayon fibers, cellulosic fibers, or peat moss, or mixtures thereof, or acrylic fibers, or the like. Cellulosic fibers include wood pulp fibers, cotton linters, and the like. Other cellulosic fibers that might be used are rayon fibers, flax, hemp, jute, ramie, cotton and the like. Combinations of fibers and fabric can be formed in many different ways so long as the absorbent unit will absorb at least about five milliliters per gram of weight of the absorbent unit. The absorbent unit preferably is from about 50 mils to about ¼ inch in thickness. Most preferably, the absorbent unit is from about 80 mils to about 200 mils in thickness. Preferably, the absorbent unit will contain superabsorbent. The superabsorbent is present either on the resilient fibers or placed with any cellulosic fibers that are present or both and is generally a water-insoluble, water-swellable polymeric substance capable of absorbing water in an amount which is at least 10 times the weight of the substance in its dried form.

The superabsorbent is in the form of fibers, spheres, particles, bits of film, globules, webs, film, foam or the like, or may be applied in the form of a liquid monomer solution which is subsequently polymerized. The superabsorbent prepared by polymerization of a monomer solution placed on fibers in a web is most frequently in the form of globules and bits of film-like particles in the web structure.

One type of superabsorbent material provides particles or fibers which may be described chemically as having a backbone of natural or synthetic polymers with hydrophilic groups or polymers containing hydrophilic groups being chemically bonded to the backbone or an intimate mixture therewith. Included in this class of materials are such modified natural and regenerated polymers as polysaccharides, including for example, cellulose and starch and regenerated cellulose which are modified by being carboxyalkylated, phosphonoalkylated, sulfoalkylated, or phosphorylated to render them highly hydrophilic. Such modified polymers may also be cross-linked to improve their water-insolubility.

These same polysaccharides may also serve, for example, as the backbone on to which other polymer moieties may be bonded by graft copolymerization techniques. Such grafted polysaccharides and their method of manufacture are described in U.S. Pat. No. 4,105,033 to Chatterjee et al. and may be described as polysaccharide chains having grafted thereon a hydrophilic chain of the general formula:

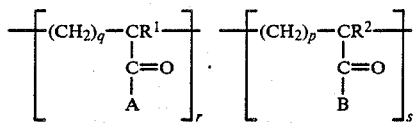

wherein A and B are selected from the group consisting of —OR³, —O(alkali metal), —OHNH₃, —NH₂, wherein R¹, R², and R³ are selected from the group consisting of hydrogen and alkylene having 1 to 4 or more carbon atoms wherein r is an integer having a value of 0 to about 5000 or more, s is an integer having a value of 0 to about 5000 or more, r plus s is at least 500, p is an integer having a value of 0 or 1, and q is an integer having a value of 1 to 4. The preferred hydrophilic chains are hydrolyzed polyacrylonitrile chains and copolymers of polyacrylamide and polysodium acrylate.

In addition to the modified natural and regenerated polymers, the hydrocolloid component may comprise wholly synthetic hydrophilic particles. Examples of those now known in the art are polyacrylonitrile fibers which may be modified by grafting moieties thereon such as polyvinylalcohol chains, polyvinyl alcohol itself, hydrophilic polyurethane, poly(alkyl phosphonates), partially hydrolyzed polyacrylamides (e.g., poly(N-N-dimethylacrylamide), sulfonated polystyrene, or a class of poly(alkyleneoxide). These highly hydrophilic synthetic polymers may be modified by other chemical treatments such as cross-linking or hydrolysis. Further examples known in the art are the non-ionic polymers such as polyoxyethylene, polyoxypropylene, and mixtures thereof which have been suitably cross-linked, either chemically or by irradiation. Still another more recent type is a derivative of isobutylnemalic and acrylate monomers, such as sodium, potassium, ammonium, (or a combination of cations), acrylate, may be placed on the absorbing layer by spraying or otherwise placing a solution thereon, followed by polymerization and cross-linking, for example, by irradiation.

In addition, naturally occurring materials such as gums may be used. Examples of such suitable gums include guar gums, acacia gums, locust bean gums and the like.

The superabsorbent can be placed between the surface of the film and the absorbent unit so long as a sufficient amount of the surface of the absorbent unit is in contact with the initially molten film to provide substantial lamination.

The extensible fabric, which is at least on the side of the absorbent unit and covers the absorbent unit to provide a liquid-permeable facing, is extensible by at least 25% and preferably up to about 100%. The fabric need be extensible in one direction only, provided that that direction provides extensibility transverse to the longitudinal axis of the diaper product. If the fabric is not extensible in and unto itself, parallel staggered rows of slits may be provided in the regions of the fabric wherein extensibility is desired. This type of extensibility is illustrated in FIGS. 4 and 5. Particularly, suitable fabrics include a fabric made of fusible fibers such as polyethylene, polypropylene and the like with up to about 50% polyester fibers, or a nonwoven thermal bonded fabric of bicomponent fibers, such as ENKA fabric by American Enka Corporation which is a sheath-core polyethylene-polyester nonwoven fabric which is thermal bonded. Other fabrics having an extensibility of at least about 25% are suitable.

The fabric may be on both sides of the initially molten elastic film. In this instance, the absorbent product which is formed has a cloth-like feel.

The method for making the absorbent article of the present invention includes bringing the absorbent unit and the fabric in contact with the initially molten film while the film is still molten (tacky). In the case of non-pressure-sensitive adhesive films it is necessary that the film still be substantially in a hot state. However, with use of a pressure-sensitive film, the film may be made first and the fabric and absorbent unit combined with it at a later time. There are basically two extrusion type processes which can be used. The first of these is what might be called a "true" extrusion wherein all of the components to form the film are placed in the extruder where they are melted, mixed and extruded through a die at pressures, temperatures and conditions to provide a film having a viscosity of 10,000 centipoises up to about 2 million centipoises at 350° F. Another method is used when preparing the hot melt pressure-sensitive adhesive wherein the hot melt mix is prepared first and is then placed through an extruder to form the film or is coated onto the substrate by use of a positive displacement pump and an extrusion die. The latter approach requires film formers having a relatively low viscosity.

The product of the present invention is soft, pliable, thereby flexible, noiseless and provides a substantially 100% stable product. Furthermore, improved absorbency and wicking ability have been observed in the product.

Another advantage of the process and the product of the present invention is the ability to add additional components, such as elastic stretch elements in the margins to gather the product. While the initially molten film is still tacky, elastic can be placed between the film and the fabric prior to final lamination. Preferably the elastic is stretched, placed in contact with the film, the fabric is placed over the elastic and lamination subsequently takes place. While the elastic is still in a stretched condition, the elastic is absolutely bonded and will not become dislodged during storage or use of the absorbent product.

The flexibility of the manufacturing techniques which are used in making the product of the present invention permits the easy addition of discrete elastic pieces or of discrete fabric pieces which may extend beyond the margins of the laminated product. For instance, a rectangular product consisting of initially molten flm, an absorbent unit smaller than the size of the film and a fabric coextensive with the film could have laminated, between the fabric and the film in the margins, pieces of fabric which extend beyond the rectangular shape of the absorbent article so as to provide a T-shped and "I" configuration or other designs.

Other advantages afforded by the present invention include multiple-article productions lines which accommodate more than one line of product through a single unit for production. Also, modification of a product in the production line is made with ease and at minimal cost. The absorbent unit can be prepared off-line and consequently will not impede the speed with which the manufacturing can take place. Likewise, other components which are to be placed in the extruded initially molten elastic film can be prepared from other production lines and then readily combined with the initially molten elastic film while it is still in its tacky state. The present invention further provides small articles which can be stretched at the time of use to provide a larger article. Products can be produced in a rectangular shape but when used stretch and form other shapes. Also the product easily conforms to the shape of the body. For instance, a wound dressing will conform to the shape of the elbow or knee.

Examples of methods of preparing the absorbent structure of the present invention are as follows. These examples are not intended to be limiting in any way and extensions and modifications thereof, without departure from the spirit and scope of the invention, will be apparent to one skilled in the art.

EXAMPLE 1

An absorbent unit is formed of polyester fibers by dry laying the fibers, i.e., by air laying or carding to form a web. Specifically, the polyester fibers contain a minor portion of fusible fibers which soften at a lower temperature than the rest of the fibers. The web is heat bonded by passing air at a temperature of 350° F. through the web for about 10 seconds. The resulting web is 25 grams per square meter, basis weight. The specific polyester fibers used are identified as Type 99 Hollofil fibers manufactured and sold by E.I. Dupont Company. The fibrous web is placed on top of a sheet of wet-formed chemically delignified wood pulp fibers, the fibers being identified as RayFloc JLD manufactured by ITT Rayonair having a basis weight of 50 grams per square meter. A powdered superabsorbent polymer is uniformly sprinkled onto and into the nonwoven fiber polyester structure at a concentration of 200 grams per square meter. The particular superabsorbent used is identified as Permasor 10 manufactured by National Starch and Chemical Corporation. The structure is sprayed with a mist of water on the polyester side and then subjected to a compression force of 640 psi for 30 seconds. On release of the pressure the structure remains compressed and is available to function as an absorbent unit.

A molten film alloy consisting of 42 parts by weight of poly(ethylene terephthalate co-ethylene azelate) and 58 parts by weight of Kraton 1107 is prepared.

While the molten film alloy is in its drawn molten state the previously prepared absorbent unit, which is narrower than the film, is placed in contact with the film and a polyester nonwoven fabric having a weight of about 0.7 oz./sq. yd. is placed over the absorbent unit and is substantially coextensive with the film. The absorbent unit and the fabric are laminated to the molten film.

Conventional adhesive tape tabs are added at each side edge of the film toward one end of the final severed diaper product.

EXAMPLE 2

An absorbent unit is prepared using the same polyester fibrous web formed in Example 1, the web is coated by flooding it with an aqueous solution of 38% solids, the solution solids being 90% sodium acrylate and 10% acrylic acid. Excess solution is drained from the web. The web is then subjected to 6 megarads of electron beam radiation after which about 70 grams/m$^2$ of PSA is present. The web is again flooded, drained and irradiate to yield a total of about 140 gm/m$^2$ PSA. A third time after flooding and draining, the web is subjected to 12 megarads of electron beam radiation to polymerize and crosslink the monomer and form polysodium acrylate (PSA) affixed to the polyester fiber. Two hundred grams/m$^2$ of PSA is present in the substrate. This is equivalent to 800% dry-add-on. This coated substrate is passed beneath a hammer mill that deposits chemically treated wood pulp fibers onto the polyester web. Vacuum is applied under the polyester web so as to cause some of the pulp fibers to at least partially migrate into the polyester web and become integral therewith. The major portion of the wood pulp fibers will reside on the surface providing a layer containing wood pulp fibers of 50 gms/m$^2$. The surface of the pulp layer is sprayed with water so that the total moisture content of the pulp is 10% by weight. This structure is compressed at a level of 640 psi for 30 seconds. Upon release of pressure the pulp has formed into a high density layer with a capillary size suitable for liquid wicking and the resilient fiber layer remains compressed. Upon use of this structure when a significant amount of liquid contacts the surface and migration of the liquid into the product takes place, the superabsorbent becomes soft and releases the resilient fibers so that the thickness of the absorbent structure increases markedly. This provides an area for storage of liquid wherein the capillary size is large.

Particulate components for an elastomeric extrudable film are placed in the feed hopper of an extruder. These components are 97 parts by weight of a styrene-isoprene-styrene elastomer Kraton 1107, 2 parts butyl zimate and 1 part Santovar. Kraton 1107 copolymer is a thermoplastic elastomeric A-B-A (styrene-isoprene-styrene) block copolymer offered by the Shell Chemical Company, wherein the styrene content (that of the A blocks) is about 12–15%, closer to 15% by weight of the block copolymer and the polymer possesses a solution viscosity of about 2,000 centipoises at 25% solids in toluene at room temperature (using a Brookfield Viscometer with a No. 4 spindle at 60 r.p.m.), and a number average molecular weight of about 110,000–125,000. The butyl zimate and Santovar are antioxidants.

A thin film, about 2 mils thick, is extruded and while the film is in a molten state the absorbent unit and a spun-bonded polypropylene nonwoven facing fabric is placed over the absorbent unit, as in Example 1, and the product is laminated. As before, appropriate tape tabs are affixed to the side edges of the product. The resulting diaper product weighs about 35 grams and holds up to at least about 150 mls. of liquid.

EXAMPLE 3

In this example, pressure-sensitive adhesive films are extruded or applied by hot melt coating techniques to provide a product to which components can be added after the film is no longer molten. To make a diaper product a soft fabric is laminated to one side of the film. On the other side of the film an absorbent unit covered with a liquid-permeable fabric or film is laminated to the film. The fabric is substantially, co-extensive with the film whereas the absorbent is smaller, preferably around the entire periphery, than the film. Another advantage of the pressure sensitive adhesive (PSA) film is that it eliminates the necessity of adding a closure to the product. For instance, the product of FIG. 1 shows the film exposed on the diaper "ears" to provide a PSA closure. Also in FIG. 3, a sanitary napkin is depicted which for the securing means shows a portion of PSA film exposed on the underside to provide securement to the clothing of the user.

Two suitable formulations for PSA film appear below:

TABLE I

|  | Kraton 1107 | Wing Tack 95 | Butyl Zimate | Santovar A |
|---|---|---|---|---|
| Sample A | 100 | 80 | 2 | 1 |
| Sample B | 100 | 140 | 2 | 1 |

In Table I above, all parts are given in parts by weight. Sample A is a PSA film which is extruded onto a substrate or onto a conveyor after which other components are added later. Sample B may be applied by extrusion or by hot melt coating techniques.

The foregoing is intended as illustrative of the present invention but is not intended as limiting in any way. Numerous variations and modifications may be made without departing from the true spirit and scope of the invention.

What is claimed:

1. An elastic, laminated disposable diaper comprising: a liquid-impermeable backing comprised of a pressure sensitive film having an outer backing fabric laminated to said elastic film, said backing fabric having at least about 25% extensibility, an absorbent core and a liquid-permeable facing comprised of fabric having at least about 25% extensibility and being coextensive with said backing, said absorbent core being laminated between said facing and said backing.

2. The disposable diaper of claim 1 wherein said absorbent core is comprised of a loosely compacted cellulosic fibrous bat.

3. The disposable diaper of claim 1 wherein said pressure sensitive film is a hot melt adhesive.

4. The disposable diaper of claim 1 wherein said initially molten film is a foam.

* * * * *